United States Patent [19]

Suida

[11] Patent Number: 5,311,985
[45] Date of Patent: May 17, 1994

[54] HOLDER FOR HYPODERMIC SYRINGES

[76] Inventor: Eleanor F. S. Suida, 2915 N. Steves Blvd., Flagstaff, Ariz. 86004

[21] Appl. No.: 100,210

[22] Filed: Aug. 2, 1993

Related U.S. Application Data

[63] Continuation of Ser. No. 894,868, Jun. 8, 1992, abandoned.

[51] Int. Cl.⁵ .................. B65D 85/24; B65D 81/22
[52] U.S. Cl. ........................... 206/210; 206/366
[58] Field of Search ............ 206/366, 365, 813, 523, 206/210

[56] References Cited

U.S. PATENT DOCUMENTS

| 1,280,687 | 10/1918 | Dudley | 206/210 |
|---|---|---|---|
| 4,380,292 | 4/1983 | Cramer | 206/813 X |
| 4,726,466 | 2/1988 | Cooper | 206/366 |
| 4,735,311 | 4/1988 | Lowe et al. | 206/365 |
| 4,748,125 | 5/1988 | Pizzolante | 206/813 X |
| 4,813,538 | 3/1989 | Blackman | 206/210 |
| 4,844,249 | 7/1989 | Coulombe | 206/366 |
| 4,919,264 | 4/1990 | Shinall | 206/366 |
| 4,969,554 | 11/1990 | Sawaya | 206/210 |
| 5,007,535 | 4/1991 | Meseke et al. | 206/366 |
| 5,047,019 | 9/1991 | Sincock | 206/366 |
| 5,160,324 | 11/1992 | Halbach | 206/366 |
| 5,190,169 | 3/1993 | Sincock | 206/366 |

FOREIGN PATENT DOCUMENTS 2227428  4/1980  Fed. Rep. of Germany ...... 206/366

*Primary Examiner*—William I. Price
*Attorney, Agent, or Firm*—S. Michael Bender

[57] ABSTRACT

A protective device for hypodermic syringes capable of avoiding needlestick injuries comprises a sterile penetrable support member and a plurality of hypodermic syringe protective caps received in the support member. In an alternative embodiment, the support member is removably attached to a base member so that it (the support member) may be disposed of and replaced by a new, sterile support member.

8 Claims, 4 Drawing Sheets

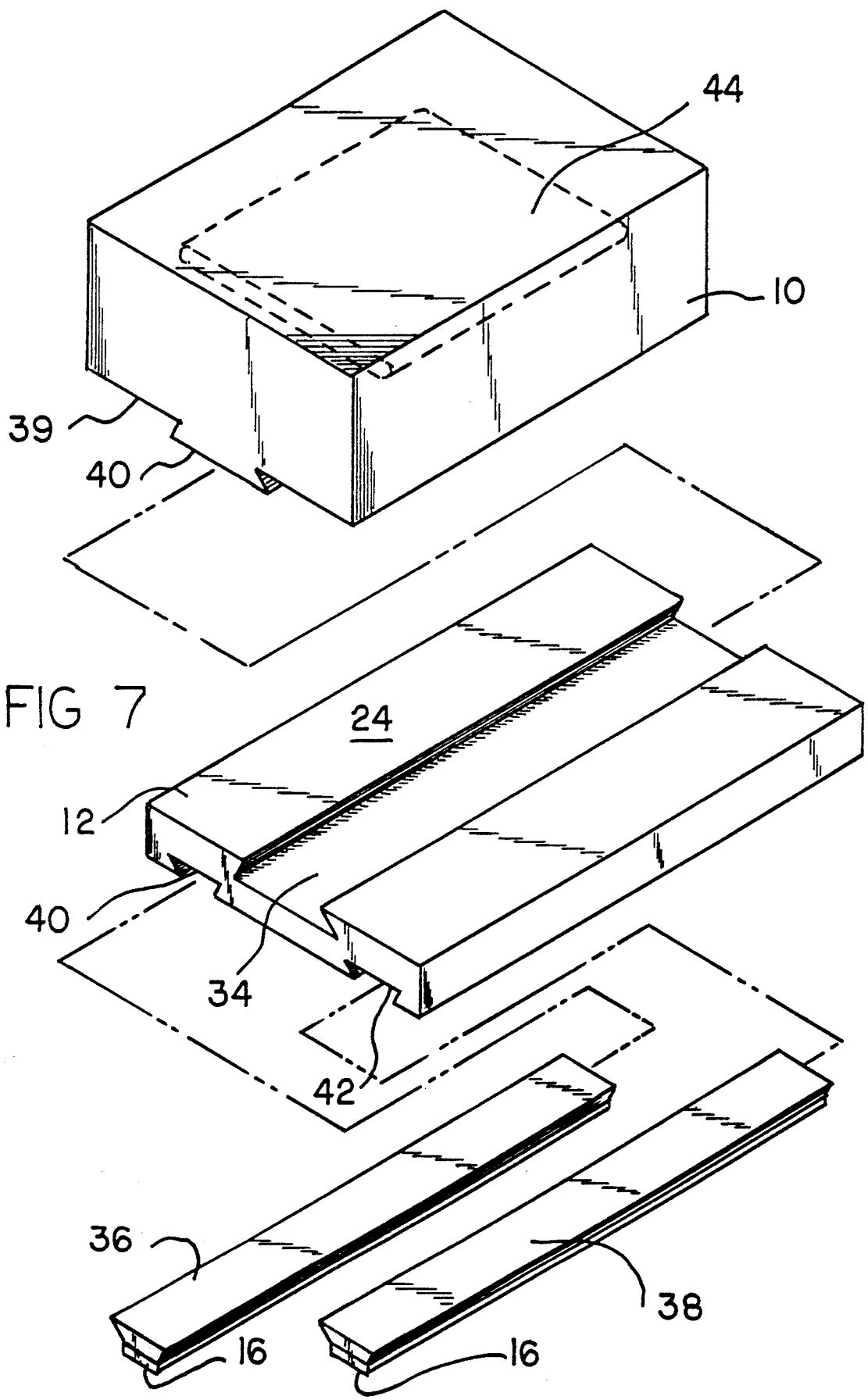

HOLDER FOR HYPODERMIC SYRINGES

This application is a continuation of application Ser. No. 07/894,868, filed Jun. 8, 1992, now abandoned.

BACKGROUND OF THE INVENTION

1. Field of the Invention

The present invention relates generally to protective devices for hypodermic syringes and more particularly, to a holder for multiple hypodermic syringes capable of avoiding needlestick injuries.

2. Description of the Prior Art

The problem of preventing so-called "needlestick" injuries to medical personnel handling hypodermic syringes has been widely addressed in the prior art. Such injuries are frequent and particularly dangerous due to the possibility of spreading contagious or infectious diseases such as AIDS. A needlestick injury occurs when medical practitioners accidentally stick themselves on an uncapped, unprotected hypodermic syringe usually following injection of the solution contained in the syringe. Often the "needlestick" occurs when an attempt is made to recap the exposed needle of the syringe, or when reaching for a surgical instrument on a tray. A popular solution to this problem is to provide a protective device for the cap or the syringe needle. Thus, for example, U.S. Pat. No. 4,919,656 discloses a disk having a central aperture through which a hypodermic needle syringe protective cap is frictionally received. Failure to emplace the needle in the cap opening results in the needle harmlessly hitting the disk rather than striking the fingers of the person handling the syringe. A similar protective device in the shape of a truncated conical shield is disclosed in U.S. Pat. No. 4,747,835.

Another solution comprises the provision of a slidable protective barrel on the syringe which may be slid into position over the exposed needle following injection and use of the syringe. Examples of this type of protective device are disclosed in U.S. Pat. Nos. 4,747,837 and 4,898,590.

Still yet another attempt to minimize "needlestick" injuries is shown in U.S. Pat. No. 4,802,645 wherein a holder for the syringe is provided having a clamp for securing the syringe's protective cap in an horizontal position adjacent a dentist's chair. Hence, the dentist does not have to hold the cap in one hand when the used syringe is recapped by the other hand, a situation which frequently results in a "needlestick."

Nonetheless, it will be appreciated that although the foregoing prior art devices purport to reduce somewhat the risk of needlstick injuries, there still exists a need for a simpler, less expensive, and generally, more improved protective device for hypodermic syringes, particularly one which is capable of facilitating the use of multiple hypodermic syringes at the same time as would be required, for example, by an anesthesiologist during a surgical procedure, or by a nurse administering several different injections to a group of patients, respectively, during rounds on a ward.

SUMMARY OF THE INVENTION

Briefly described, the new and improved holder for hypodermic syringes according to the present invention comprises a sterile block of penetrable material in which a multiplicity of capped hypodermic syringes may be embedded. The block which serves as a support member for the syringes or for needle caps for syringes is fixedly secured to a base member which, in turn, may temporarily be fixed securely to a work surface such as a tray carrying surgical instruments, for example. In an alternative embodiment, the support member is removably attached to the base member so that it may easily be removed and replaced by a fresh, sterile support member. In addition, reservoir means containing a disinfecting medium are located within the support member rupturable upon penetration by a hypodermic needle or needle cap to release the disinfecting medium into the support member.

The above brief description sets forth rather broadly the more important features of the present invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least two embodiments of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

Further, the purpose of the foregoing Abstract is to enable the U.S. Patent and Trademark Office and the public generally, and especially the scientists, engineers and practitioners in the art who are not familiar with patent or legal terms of phraseology, to determine quickly from a cursory inspection the nature and essence of the technical disclosure of the application. Accordingly, the Abstract is neither intended to define the invention of the application, which only is measured by the claims, nor is it intended to be limiting as to the scope of the invention in any way.

It is therefore an object of the present invention to provide a new and improved holder for hypodermic syringes which has all the advantages of the prior art and none of the disadvantages thereof.

It is another object of the present invention to provide a new and improved holder for hypodermic syringes which may be easily and efficiently manufactured and marketed.

It is a further object of the present invention to provide a new and improved holder for hypodermic syringes which is of a durable and reliable construction.

An even further object of the present invention is to provide a new and improved holder for hypodermic syringes which is susceptible of a low cost of manufacture with regard to both materials and labor, and which accordingly is then susceptible of low prices of sale to the consuming public, thereby making such holder for hypodermic syringes economically available to the buying public.

Still yet another object of the present invention is to provide a new and improved holder for hypodermic syringes which provides in the apparatuses and methods of the prior art some of the advantages thereof, while simultaneously overcoming some of the disadvantages normally associated therewith.

Still another object of the present invention is to provide a new and improved holder for hypodermic syringes capable of supporting a multiplicity of hypodermic syringes in a manner avoiding needlestick injuries.

Yet still another object of the present invention is to provide a new and improved holder for hypodermic syringes having a support member easily capable of being replaced with a fresh, sterile support member.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had now to the accompanying drawings and descriptive matter in which there are illustrated preferred embodiments of the invention.

BRIEF DESCRIPTION OF THE DRAWINGS

The invention will be better understood and the above objects as well as objects other than those set forth above, will become apparent when consideration is given to the following detailed description thereof. Such description makes reference to the annexed drawings wherein:

FIG. 7 is an exploded view in perspective of the alternatively preferred embodiment of FIG. 5 showing the parts thereof unassembled.

DESCRIPTION OF THE PREFERRED EMBODIMENT

With reference now to the drawings, a new and improved holder for hypodermic syringes embodying the principles and concepts of the present invention will be described.

Figure 1:
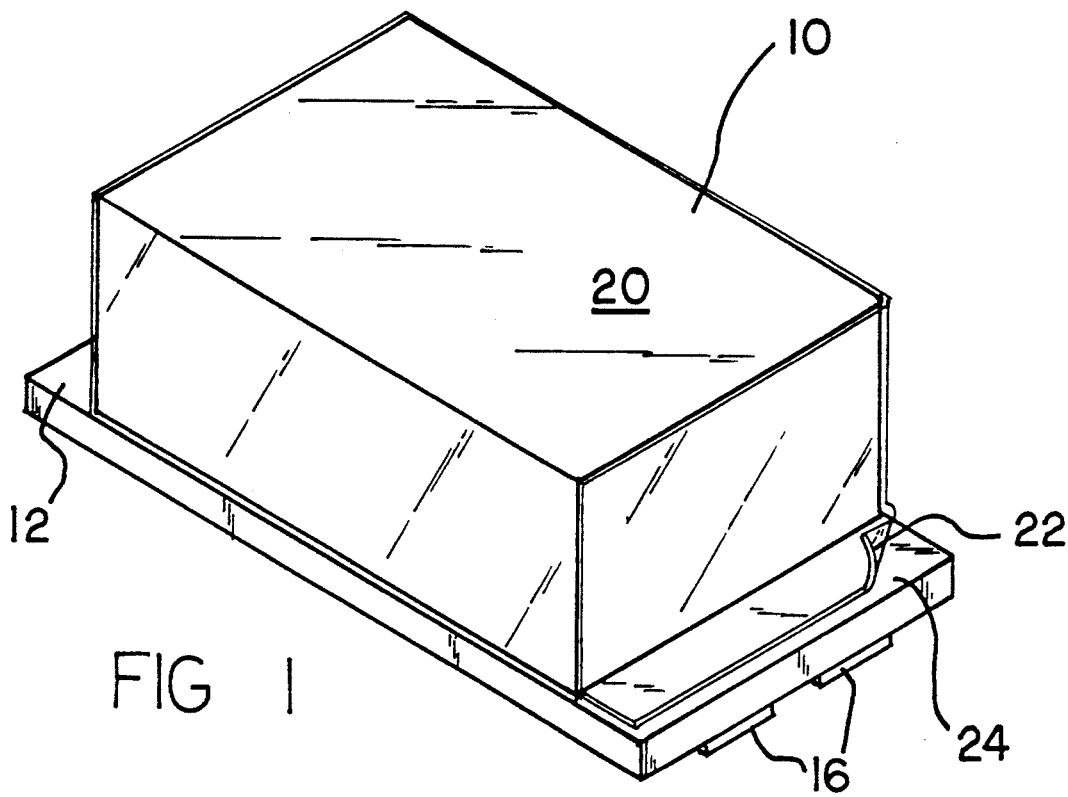
FIG. 1 is an perspective elevational view of a new and improved holder for hypodermic syringes according to the present invention.
Figure 2:
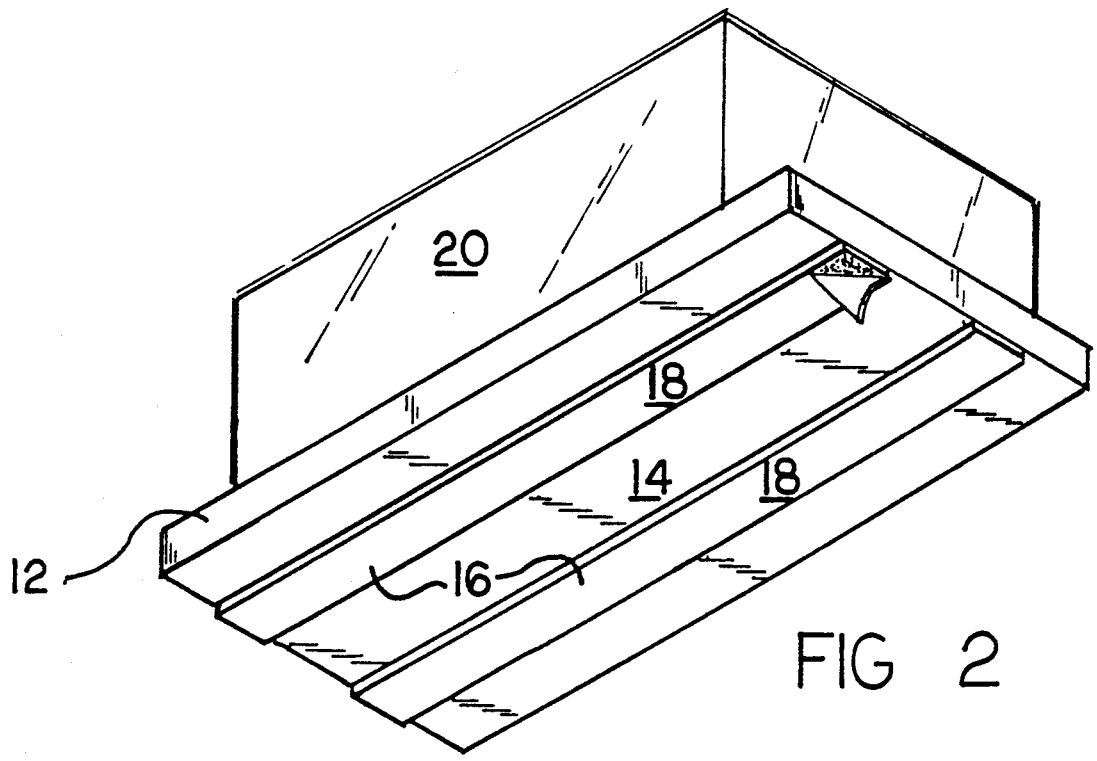
FIG. 2 is a perspective elevational view showing the bottom mounting surface of the base of the invention of FIG. 1.

Turning initially to FIGS. 1 and 2, there is shown a first preferred embodiment of a syringe holder unit of the present invention comprising a rectangularly shaped block 10 of sterile, inert, penetrable and spongy material which, as will be further explained in detail below, is capable of receiving and supporting a capped hypodermic syringe embedded therein. Thus, block 10 serves as a support member for a multiplicity of hypodermic syringes much like a "pin-cushion" serves as a support member for a multiplicity of pins, needles, or other sharply pointed objects. A material for block or support member 10 which has been found to be especially suitable is a conventional open cell styrofoam plastic and therefore is mostly preferred. However, other known materials capable of receiving the capped needle of a conventional hypodermic syringe (the details of which are outside the scope of this invention), or the exposed needle of such a syringe, in frictional supporting engagement may be employed instead. Suffice it to say, the material of support member 10 must be such that the cap of a hypodermic syringe may be embedded therein with a minimum of force, and the material must furthermore, frictionally grip or retain the embedded cap sufficiently to (i) support the hypodermic syringe in an upright manner, and (ii) retain the needle cap secured therein when the hypodermic syringe and needle is withdrawn from the cap. The material should also similarly support the hypodermic syringe should its needle be embedded therein without the cap.

Support member or block 10, in turn, is fixedly attached by using a suitable adhesive, for example, to a rectangularly shaped base member 12 whose longitudinal or major dimension preferably extends beyond either side of support member 10 substantially as shown. Advantageously, base member 12 may be fabricated of stiff durable material such as aluminum, for example. Located on the bottom surface 14 of base member 12 is a pair of conventional tacky adhesive strips 16 covered by a wax-paper protective film 18. The adhesive strips preferably are arranged in a spaced, parallel manner substantially as shown; however, it will be understood that alternatively, a single pad of tacky adhesive material covered by a single film of protective material substantially covering the entire bottom surface 14 of base member 12 may be employed instead. In use, the protective film 18 is peeled away exposing the tacky adhesive strips 16 and permitting the base member 12 to the press-fit onto a supporting surface such as a surgical tray, for example, with the support member or block 10 facing upward (FIG. 1) and the entire unit (comprising support member 10 and base 12) remaining securely fixed thereon.

In accordance with the invention, support member 10 must be sterile before use and in order to assure this condition is completely covered in a suitable manner with a protective shield in the form of a thin flexible film or layer 20 which may be removed by a nurse or doctor merely by peeling tab section 22 away from upper surface 24 of base member 22 and removing the remainder of the film. Film 20 preferably is fabricated from a transparent plastic material (e.g. polyethylene), but other known similar materials may be used to completely cover and preserve the sterile quality of support member 10 until the syringe holder unit is to be used.

Figure 3:
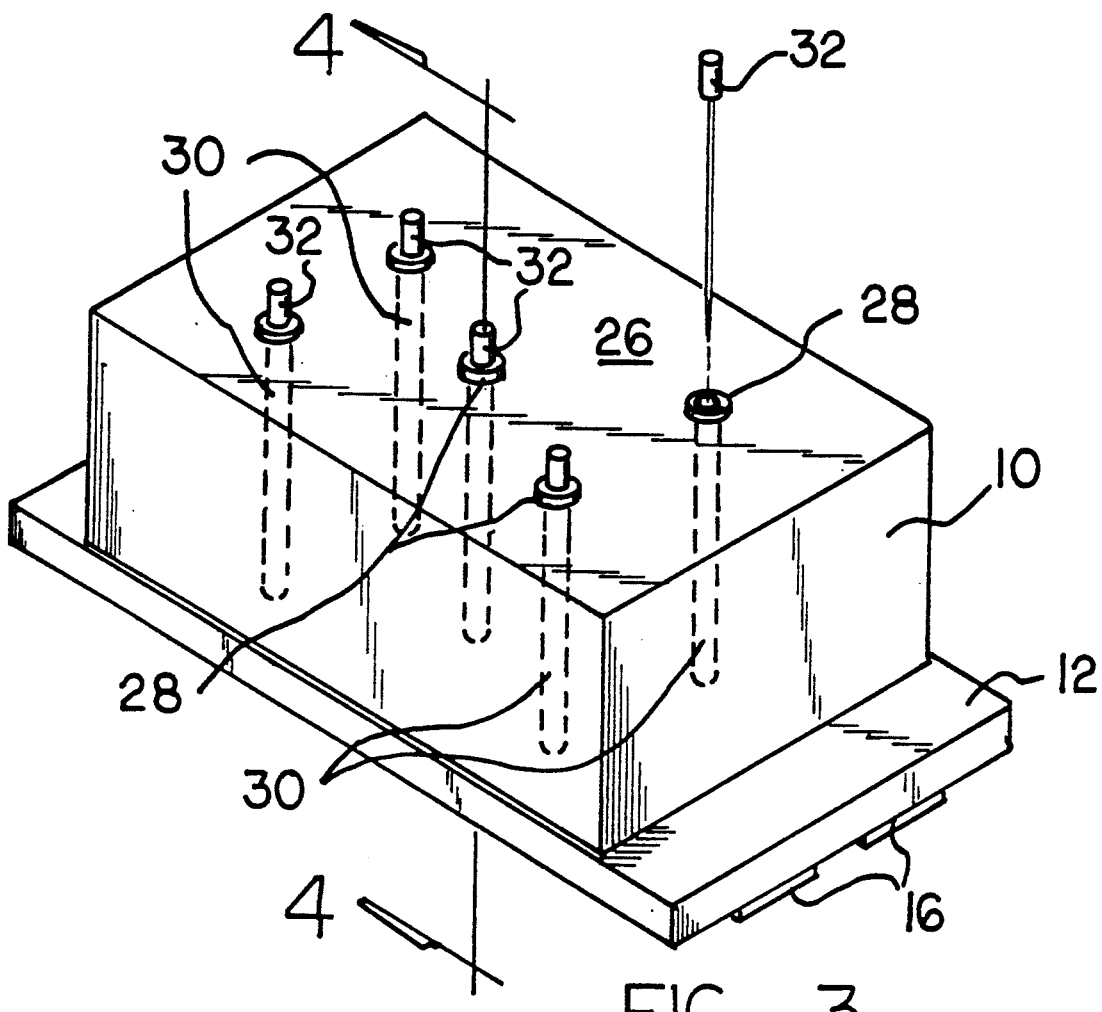
FIG. 3 is a perspective elevational view of the invention of FIG. 1 showing a multiplicity of hypodermic syringe needles embedded therein.
Figure 4:
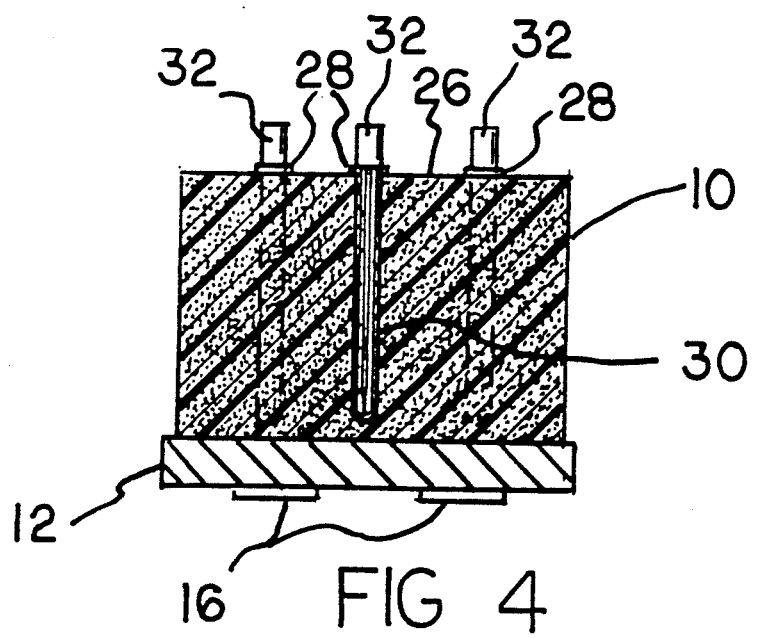
FIG. 4 is a cross-sectional view in elevation of the invention of FIG. 3 taken along line 4—4 thereof.

Turning now to FIGS. 3 and 4, there is shown the syringe holder unit of the present invention in position for use after the sterile-protective film 20 has been removed and the base member 12 affixed to a work surface in a medical environment. In one mode of use, a multiplicity of conventional hypodermic syringes having capped needles are speared into top surface 26 of support member 10. That is, each syringe needle cap is embedded in the yieldable material of the support member until the collar 28 of the cap 30 bears against surface 26. Because the material of the support member 28 is yieldable but still capable of frictionally gripping the embedded cap, this action will securely support the syringe, the syringe needle, and the cap in place until the syringe is used. Although omitted from the drawings for the sake of clarity, each hypodermic syringe will be attached to a corresponding needle 32 and will extend upwardly from the support member in an easy-to-grasp manner. Thus, should an anesthesiologist, for example, require a plurality of injectable drugs during a surgical procedure, the corresponding syringes will be emplaced in the support member 10 prior to commencing the procedure. When a particular syringe is needed, it may be withdrawn from its corresponding embedded cap 30, used to inject a liquid drug, and then re-inserted into the empty cap still embedded in surface 26 (see FIG. 3). Should the person handling the syringe miss the opening at the top end of the cap upon re-insertion the syringe needle will merely enter the material of support member 10 and be embedded therein. This action will support the corresponding hypodermic syringe in the upright position with the syringe needle protected nonetheless. Thus, the doctor or nurse will not have to spend valuable time attempting to locate the relatively narrow opening of the syringe needle cap during a surgical procedure when time is at a premium and the doctor or nurse is concentrating on other more critical matters. And by not having to hold the needle cap in the hand, needlestick injuries are completely avoided. When the medical procedure is over, and/or all of the syringes originally supported in member 10 have been used, the entire support member including any syringes, needles, and caps embedded therein may be disposed of in accordance with any hospital or other protocols relating to used/contaminated syringes. This will be accomplished merely by lifting base member 12 from the work surface sufficient to break the adhesion produced by strips 16 and placing the entire unit in a disposable plastic bag, or the like.

In certain applications, it may be advantageous to provide a syringe holder unit wherein the supporting block 10 may be removed easily from the base member 12 and replaced with a new, sterile member. Alternatively, it may be desirable to more easily remove the base member 12 from its supporting surface. Means for accomplishing the foregoing are included in the alternatively preferred embodiment of FIGS. 5-7 which will now be described with like parts being denoted by like reference numerals.

Disposed in top surface 24 of base member 12 is a longitudinally extending slot or channel having tapered walls to define a dove-tailed shaped slot or mortise 34. Mortise 34 is positioned substantially centrally of base member 12. Disposed on the bottom surface 39 of support member 10 and extending therefrom is a longitudinally extending spine having a dove-tailed cross-sectional shape to define a tenon 40 adapted to be received in and cooperatively engage mortise 34. Thus, support member 10 may be removably secured to base member 12 via a dove-tailed joint, as shown by sliding the leading edge of tenon 40 into mortise 34 and sliding the support member relative to the base member until the two parts are substantially centered. Removal of the two parts relative to each other may be effected by a reverse procedure.

Similar dove-tailed joints may be employed to removably secure adhesive strips 16 to the bottom surface 14 of the base member 12. Thus, a pair of tenons 36, 38 are provided adhesively secured to strips 16 along the longitudinal extent thereof. A corresponding pair of longitudinally extending mortises 40, 42 are provided in the bottom surface 14 of base member 12. By this arrangement, the tenons 36, 38 may be secured via tacky strips 16 to a mounting surface and base member 12 removably attached thereto by causing the mortises 40, 42 on base member 12 to slidably engage the tenons 36, 38.

Figure 5:
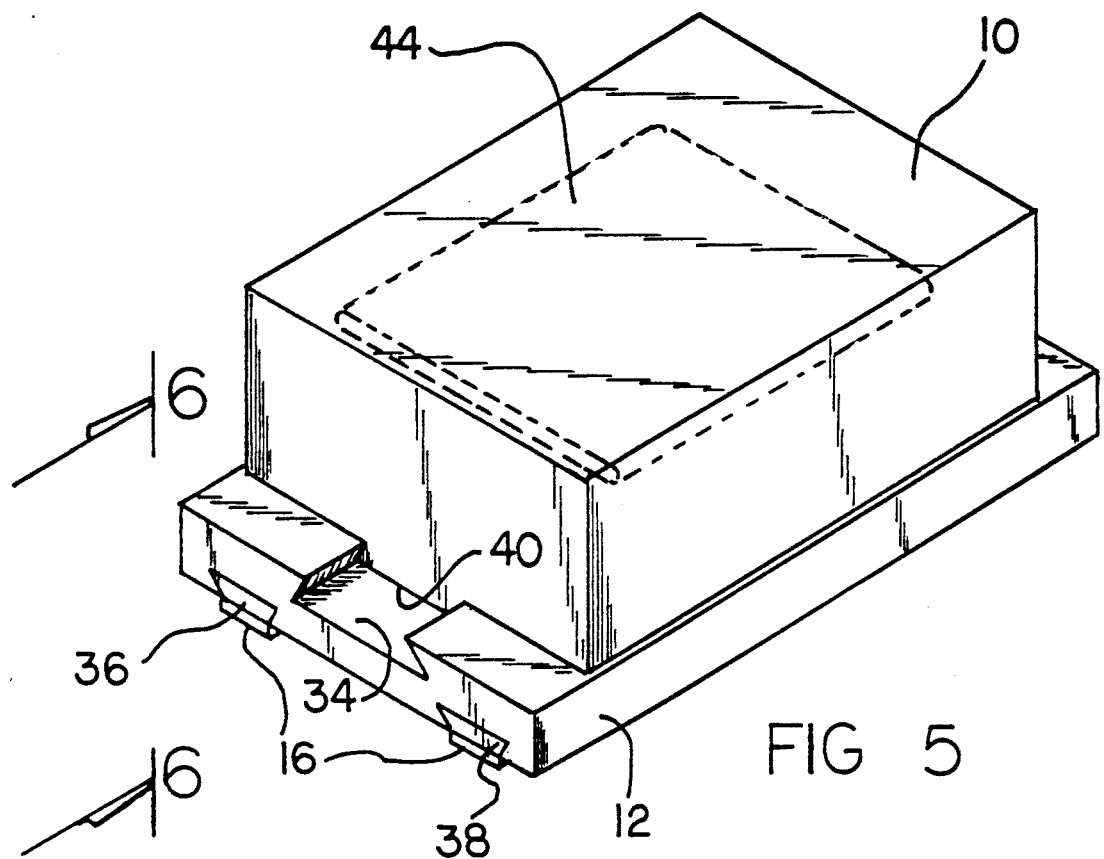
FIG. 5 is a perspective view of an alternative embodiment of the present invention.
Figure 6:
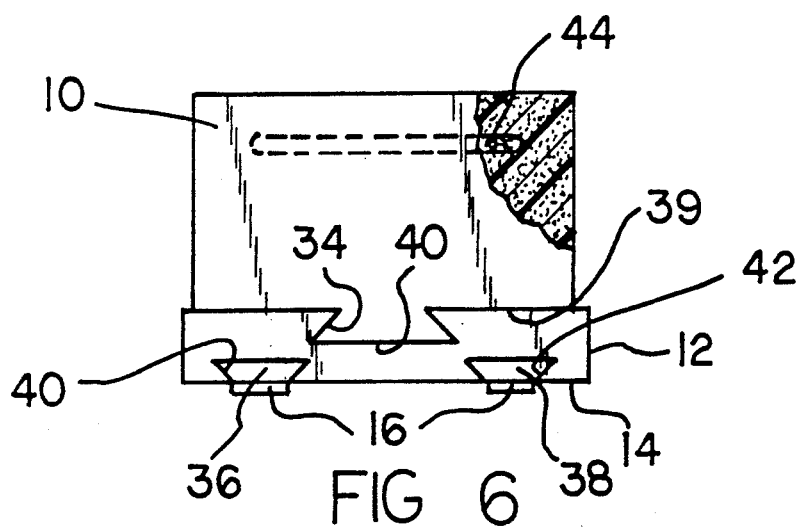
FIG. 6 is a side view in elevation partially broken away of the alternative embodiment of FIG. 5 taken along line 6—6 thereof.

Another important feature of the alternatively preferred embodiment of FIGS. 5-7 is the provision of a reservoir 44 located below the top surface of support member 10 and interiorly thereof substantially as shown. Reservoir 44 comprises a bag or pouch of flexible, suitably impervious material containing an antiseptic or disinfectant solution (e.g. alcohol). The bag or reservoir 44 is adapted to be pierced by a hypodermic syringe needle or cap being embedded into supporting member 10 as described above. The fluid from reservoir 44 will then seep into the spongy material of the support member site in and around the embedded cap or needle thereby helping to maintain the piercing hypodermic syringe part in a sterile or decontaminated condition.

In summary, there has been fully disclosed above a new and improved holder for hypodermic syringes which is capable of not only providing a convenient storage facility for hypodermic syringes awaiting use, but moreover, provides a relatively simple, and inexpensive means for avoiding frequent and potentially dangerous needlesticks thereby protecting health care providers against contagious and infectious diseases such as AIDS.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

While the present invention has been shown in the drawings and fully described above with particularity and detail in connection with what is presently deemed to be the most practical and preferred embodiment(s) of the invention, it will be apparent to those of ordinary skill in the art that many modifications thereof may be made without departing form the principles and concepts set forth. Hence, the proper scope of the present invention should be determined only by the broadest interpretation of the appended claims so as to encompass all such modifications and equivalents.

What is claimed as being new and desired to be protected by Letters Patent of the United States is as follows:

1. A new and improved holder for hypodermic syringes comprising; a supporting member, said supporting member defining a surface for receiving in a piercing and embedding manner the capped terminus of at least one hypodermic syringe, said supporting member being adapted to retain the capped terminus of said at least one hypodermic syringe embedded therein upon withdrawal of said hypodermic syringe from said capped terminus, wherein said supporting member further includes a reservoir disposed interiorly thereof, said reservoir containing antiseptic/disinfectant means therein, said reservoir adapted to be pierced and dispense said antiseptic/disinfectant into said supporting member upon being pierced by said hypodermic capped terminus or said hypodermic needle therein being embedded in said supporting member.

2. The invention of claim 1 wherein said supporting member includes means for removably attaching said supporting member to a work surface with said surface for receiving facing upwardly and away from said work surface.

3. The invention of claim 2 wherein said means for removably attaching comprises a base member, said supporting member being fixed to said base member, and said base member includes adhesive means for fixedly attaching said base member to said work surface.

4. The invention of claim 3 wherein said supporting member comprises a block of material capable of having the capped terminus of a hypodermic syringe embedded therein and capable of frictionally engaging said capped terminus and retaining same embedded therein upon withdrawal of said hypodermic syringe from said capped terminus.

5. The invention of claim 4 wherein said material is a styrofoam plastic.

6. The invention of claim 4 wherein said supporting member is in the shape of a rectangularly shaped block.

7. The invention of claim 3 wherein said supporting member includes means cooperatively engaging said base member to permit said supporting member to be releasably secured to said base member.

8. The invention of claim 1 further comprising a sterile covering on said supporting member, said sterile covering comprising a thin film of protective material completely covering said supporting member, said covering having a pull tab extending therefrom whereby said thin film may be peeled from said supporting member by pulling on said pull tab.

* * * * *